United States Patent [19]

Drewlow

[11] Patent Number: Plant 6,495

[45] Date of Patent: Dec. 27, 1988

[54] STREPTOCARPUS PLANT NAMED ELECTRA

[75] Inventor: Lyndon W. Drewlow, Ashtabula, Ohio

[73] Assignee: Mikkelsens, Inc., Ashtabula, Ohio

[21] Appl. No.: 42,103

[22] Filed: Apr. 22, 1987

[51] Int. Cl.[4] ..... A01H 5/00

[52] U.S. Cl. ..... Plt./68

[58] Field of Search ..... Plt./68

*Primary Examiner*—Robert E. Bagwill

*Attorney, Agent, or Firm*—Schwartz, Jeffery, Schwaab, Mack, Blumenthal & Evans

[57] ABSTRACT

A Streptocarpus plant named Electra, characterized by its bright red-purple flower color, rosette form with short pliable leaves, compact growth habit, ease of propagation and early flowering, highly floriferous and continuous flowering habits, and by its ability to flower both under low light and high temperature conditions.

1 Drawing Sheet

The present invention relates to a new and distinctive cultivar of Streptocarpus plant, botanically known as *Streptocarpus×hybridus,* and known by the cultivar name Electra. Electra was developed by me in Ashtabula through controlled breeding by crossing Mikkelsen Seedling 82-1093-10 (seed parent)×Mikkelsen Seedling 82-937-41 (pollen parent).

Asexual reproduction of Electra by leaf cuttings has shown that the unique features of this new Streptocarpus are stabilized and are reproduced true to type in successive propagations.

The following characteristics distinguish the new Streptocarpus from both its parent varieties and other cultivated Streptocarpus of this type known and used in the floriculture industry. Of the comparison cultivars referred to, Muse, Pegasus, Minerva, and Achilles are cultivars of applicant disclosed in pending applications.

1. Electra has numerous short leaves in a rosette instead of one large leaf that characterizes many of the older cultivars. This results in a cluster of flowers in the center of the plant making an attractive 10 cm flowing plant.

2. Electra propagates well from leaf cuttings producing numerous plantlets in 8 to 10 weeks depending on the time of the year. It is early to flower when compared with older cultivars; from a well rooted plant from a 72 cell pack a well developed flowering plant is obtained in 6 to 8 weeks in a 10 cm pot.

3. Flower color of Electra is a bright magenta with much more red pigment in the flower than Muse and Adonis, both of which are more lavender pink in color.

4. Electra is similar in height and plant spread to Pegasus and Muse, with Minerva being a dwarf and Adonis and Achilles being larger in size.

5. Leaf size of Electra is similar to Muse and Pegasus and smaller than Achilles and Adonis. Leaf color is similar to Adonis, Muse, and Achilles, but deeper green than Pegasus.

6. Flower size of Electra is smaller than Achilles, but equal to Pegasus, Muse and Adonis. The cuts between the 5 lobes of the flower of Electra are wider than Adonis, Muse and Pegasus.

7. The average number of flowers per bloom stalk on Electra is 4 which is similar to Pegasus and Muse, more than Adonis which has an average of 3, but less than Achilles which has an average of 6.

8. Electra has shown the ability to flower both under the lower light conditions of winter (December to February) and under the high temperatures of summer (July to September) without going out of bloom under greenhouse conditions.

9. Electra has the ability to tolerate watering with 40° F. water without foliar spotting and to tolerate fairly high light levels in the summer months without bronzing of the leaves.

10. Electra has leaves that are pliable making the plant easy to sleeve for shipping. Also, the flowers of Electra are long lasting and do not shatter easily. Muse, Pegasus and Achilles have similar characteristics, while Adonis does not ship as well.

The accompanying photographs illustrate the overall appearance and flower color of Electra as closely as possible. The top photograph is entirely in color and comprises a perspective view of the plant. However, the depicted flower color is not precise. The bottom photograph is an enlarged black and white, with the petals of several flowers being colored to accurately show the true flower color.

The following is a detailed description of Electra based on plants produced under commercial practices in the greenhouses of Mikkelsens Inc., Ashtabula, Ohio. Color references are made to The Royal Horticultural Society Colour Chart (RHS), except where general colors of ordinary dictionary significance are used.

Parentage: Controlled cross between Mikkelsen seedling 82-1093-10 and Mikkelsen seedling 82-937-41.

Propagation:

A. *Type cutting.*—Leaf.

B. *Time to develop plantlets.*—Summer: 8 weeks at 20° C. Winter: 10 weeks at 20° C.

C. *Rooting habit.*—Numerous, fine, fibrous.

Plant description:

A. *Form.*—Leaves rosette from a crown at the soil line. Flower stalks develop from the midrib of the leaf resulting in a cluster of flowering stalks at the center of the plant.

B. *Habit of growth.*—Compact spreading, very free flowering, never going out of bloom under greenhouse conditions. Flowers carried above foliage.

C. *Height from soil line.*—12 to 15 cm at maturity to top of blooms.

D. *Spread.*—40 to 45 cm at maturity. Leaf size: 20 to 25 cm long and 8 to 9 cm wide at the widest point; leaf size can vary greatly with cultural conditions. Quantity: Mature plant can have more than 20 leaves. Leaf shape: Elliptical. Texture: Lower surface rugose with veins protruding and pubescent; upper surface rugose and pubescent. Margin: Finely crenate. Color: Young foliage top side 137B; under side 145C. Mature foliage top side 137A; under side 145C. Ribs and veins: Pinnate. Rib and vein color: 146C. Leaf tips: Obtuse. Leaf base: Acute.

Flowering description: Flowers open one at a time on the individual flower stalks.

A. *Fully expanded.*—40 to 45 mm.

B. *Stem.*—Simple, reddish purple, round, pubescent; several flower stems develop from a leaf midrib.

C. *Form.*—Calyx deeply 5 parted with no tube; corolla cylindrical 5 lobed, lobes orbicular to obvate with 2 upper petals slightly smaller than the lower 3 petals. Upper petals reflexed, lower petals flattened to give an overall flat appearance.

D. *Flower bud description.*—20 to 23 mm at maturity, tubular with the end larger in diameter than the rest; 5 green with purple tint calyx folded over basal end.

E. *Flowers borne.*—In clusters of 3 to 4 flowers per flower stalk, with 4 the most common; carried above foliage. Pedicels vary in length, terminal flower opens first and flower stems from midrib of leaf.

F. *Quantity of flowers.*—Mature plant can have more than 20 flower stalks open, with up to 4 flowers open on each.

G. *Permanence.*—Long lasting, 10 or more days.

Color:

A. *Tonality from a distance.*—Bright magenta with white and greyed-yellow streaking from the throat.

B. *Upper surface of petals.*—74A and 74B.

C. *Reverse of petals.*—74C; 155C white group streaking from fused area of corolla to lower areas of individual petals.

D. *Throat.*—Mostly 74A. Some 155C and 161D streaking.

E. *Discoloration.*—Fades to a slightly lighter and less bright shade of magenta.

Petals:

A. *Texture.*—Satin.

B. *Appearance.*—Individually lobed with slight crenate margins; top 2 petals are reflexed and smaller than the 3 bottom petals which are flat.

C. *Arrangement.*—Regularly united into an almost circular shape and slightly cupped.

D. *Persistence.*—10 days or longer; petals remain on plant in dry form until picked.

E. *Fragrance.*—None.

Reproductive organs:

A. *Stamens.*—2 fertile, 2 sterile — very small. Anther shape: 2 fertile; interconnected and flat. Anther color: Cream with slight purple cast. Filament: Attached to petals for 20 mm; 2 sterile free standing for less than 1 mm and 2 fertile for 5 mm, the last having a purple tinge. Pollen color: Cream.

B. *Pistils.*—Stigma shape: 2 lobed flattened, with reflexed tips. Stigma color: White. Stigma size: 3 mm across. Style color: White. Style size: 7 mm. Ovaries: Numerous, 10–12 mm on a receptive pistil, purplish.

Disease resistance: No disease problems to date.

Other important characteristics: Compact growth habit with short pliable leaves combined with its highly floriferous nature makes Electra suitable for 10 cm pot plant production on a year round basis. The long lasting and non-shattering flowers and leaves, that do not scorch under high light conditions or spot when watering with cold water (40°), further enhance this cultivar. Lack of major disease and insect problems, as observed to date, makes this a trouble free crop.

I claim:

1. A new and distinct cultivar of Streptocarpus plant named Electra, as illustrated and described, and particularly characterized by its bright red-purple flower color, rosette form with short pliable leaves, compact growth habit, ease of propagation and early flowering, highly floriferous and continuous flowering habits, and its ability to flower both under low light and high temperature conditions.

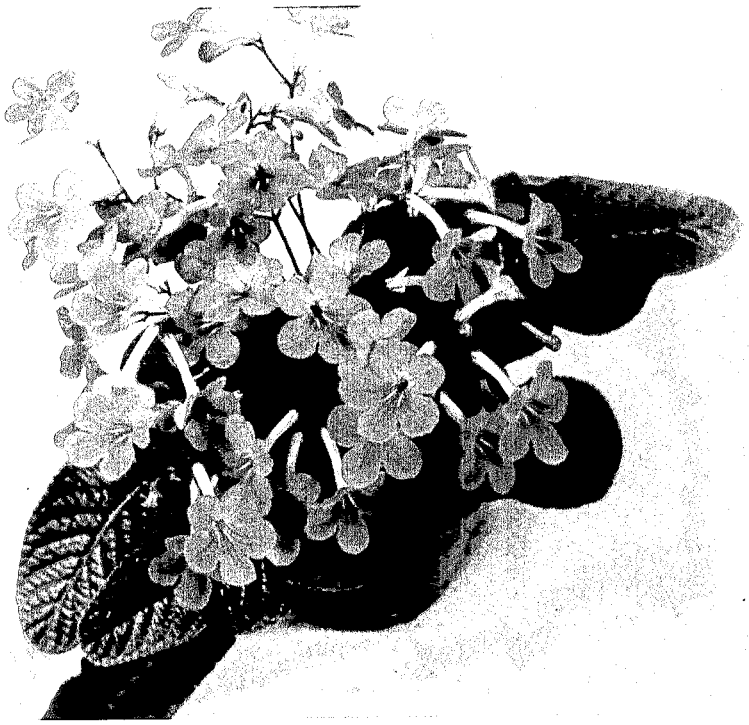
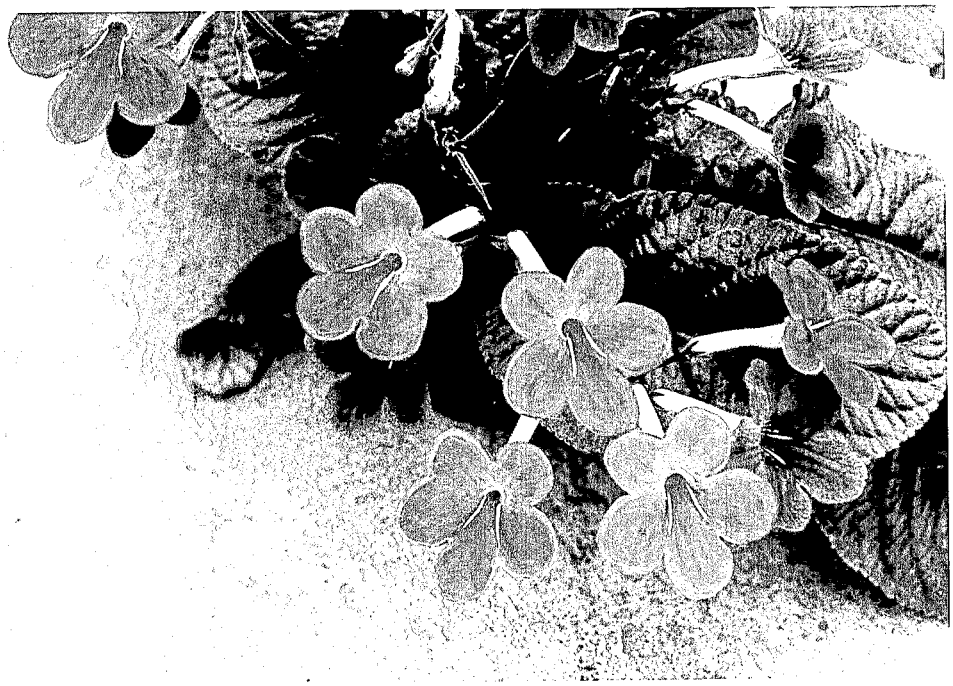

* * * * *